US00PP35782P2

(12) United States Plant Patent
Olesen

(10) Patent No.: US PP35,782 P2
(45) Date of Patent: Apr. 30, 2024

(54) FLORIBUNDA ROSE PLANT NAMED 'POULPAL103'

(50) Latin Name: *Rosa hybrida*
Varietal Denomination: Poulpal103

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 18/445,481

(22) Filed: Sep. 8, 2023

(30) Foreign Application Priority Data

Sep. 30, 2022 (QZ) ..... PBR 2022/2171

(51) Int. Cl.
*A01H 5/02* (2018.01)
*A01H 6/74* (2018.01)

(52) U.S. Cl.
USPC ..... Plt./151

(58) Field of Classification Search
USPC ..... Plt./101, 141, 151
See application file for complete search history.

*Primary Examiner* — Susan McCormick Ewoldt

(57) ABSTRACT

A new garden rose plant of the Compact Floribunda class which has abundant, red flowers and attractive foliage. This new and distinct variety has shown to be uniform and stable in the resulting generations from asexual propagation.

2 Drawing Sheets

Botanical designation: *Rosa hybrida.*

Variety denomination: 'Poulpal103'.

This application claims priority to Plant Breeder's Rights Application Number 2022/2171, which was filed at the Community Plant Variety Rights Office in the European Union on Sep. 26, 2022, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2014 and the resulting seeds were planted in a controlled environment in Fredensborg, Denmark. The new variety, named 'Poulpal103', originated as a single seedling from the stated cross.

The new variety may be distinguished from its male pollen parent and female seed parent primarily by the following characteristics. The male pollen parent plant has red flowers with a basal petal spot the colour of Green-White Group 157A while the new variety has red flowers with a yellow petal spot at the base of the petal. The female seed parent plant has deep pink flowers while the new variety has red flowers.

The objective of the hybridization of this rose variety was to create a new and distinct variety with unique qualities, such as:

1. Uniform and abundant red flowers;
2. Vigorous, but compact growth when propagated on its own roots;
3. Exceptional disease resistance.

This combination of qualities is not present in previously available commercial cultivars of this type, known to the inventor, and distinguish 'Poulpal103' from all other varieties of which we are aware.

As part of the rose development program, Mogens N. Olesen germinated the seeds from the aforementioned hybridization during winter of 2014 and conducted evaluations on the resulting seedlings in a controlled environment in Fredensborg, Denmark. 'Poulpal103' was selected in the spring of 2015 by the inventor as a single plant from the progeny of the aforementioned hybridization.

Asexual reproduction of 'Poulpal103' by rooted cuttings was first done by Mogens N. Olesen in the nursery in Fredensborg, Denmark in July, 2015. This initial and other subsequent asexual propagations conducted in controlled environments have demonstrated that the characteristics of 'Poulpal103' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpal103'.

Specifically illustrated in FIG. 1 of the drawings are an open flower viewed from above, petals detached revealing reproductive flower parts, sepals detached revealing the receptacle and pedicel, and a flower bud upon opening.

Figure 1:
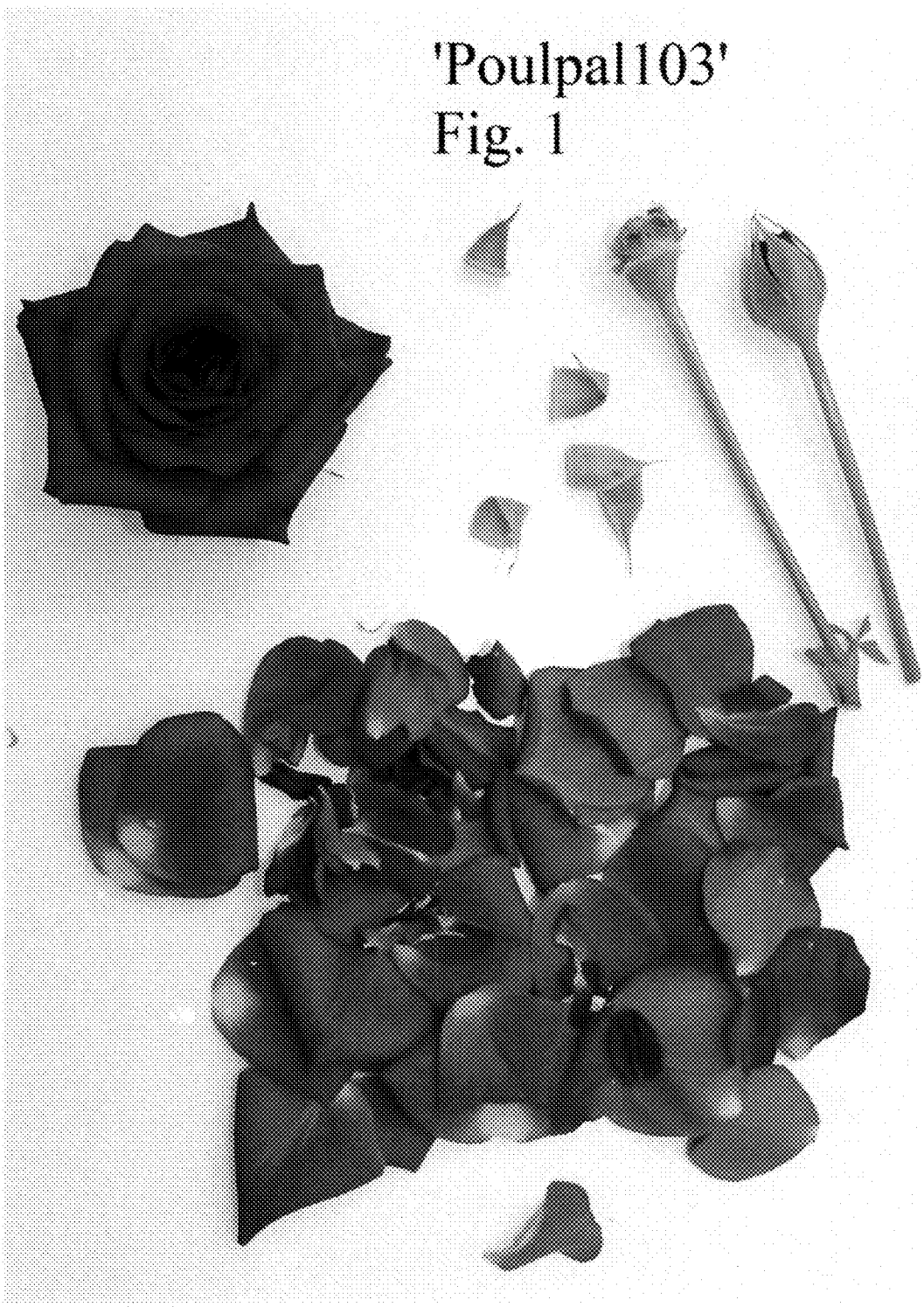
Figure 2:
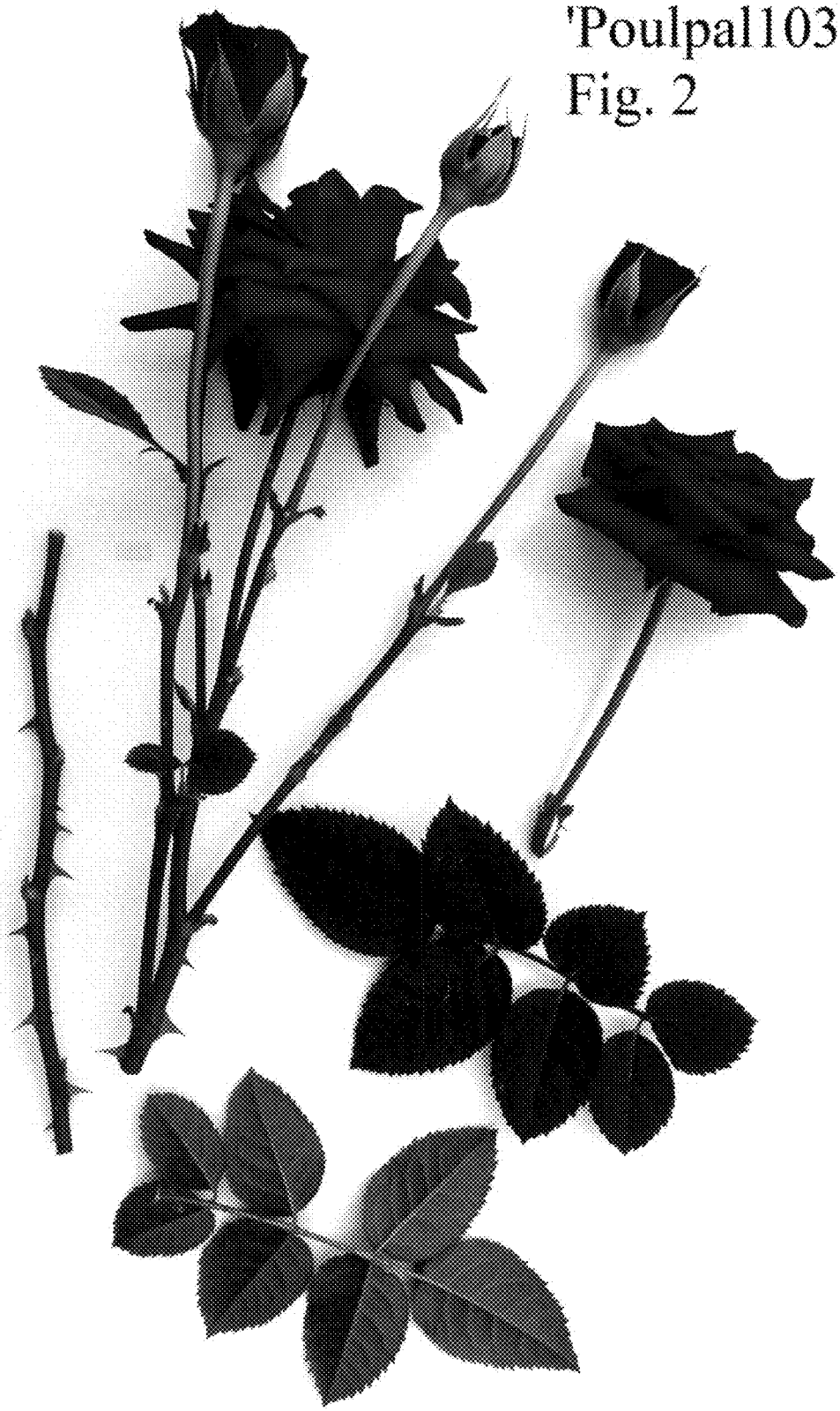

Specifically illustrated in FIG. 2 of the drawings are a cluster of flowers at various stages of opening on the branch, an open flower viewed from the side, bare stem exhibiting prickles, and mature leaves. Plants shown are 4 months old.

DETAILED DESCRIPTION OF THE VARIETY

The following is a description of 'Poulpal103', as observed in its growth in an indoor glasshouse nursery in Odense Denmark. Observed plants are 4 months of age, and were grown on their own roots in 19 cm pots. Color references are made using The Royal Horticultural Society (London, England) Colour Chart, 2001, except where common terms of color are used.

For a comparison, several physical characteristics of the rose variety 'Poulpal0590', U.S. Plant Pat. No. 27,739 are compared to the claimed plant. While 'Poulpal103' has 58 flower petals, 'Poulpal059' has 35 to 49 flower petals. The claimed plant has a flower diameter of 60 to 70 mm while 'Poulpal059' has a flower diameter of 55 mm. Open flowers of 'Poulpal103' are generally Red Group 53A in color while 'Poulpal059' has a general tonality of Red Group 46A.

FLOWER AND FLOWER BUD

Blooming habit: Continuous.

Flower bud:

- *Size.*—Upon opening, 21 mm in length from base of receptacle to end of bud. Bud diameter is 19 mm.
- *Bud form.*—Ovoid.
- *Bud color.*—As sepals divide petals are Red-Purple Group 59B.
- *Sepal inner surface.*—Color: Yellow-Green Group 146D. Surface: Lightly pubescent.
- *Sepal outer surface.*—Color: Yellow-Green Group 144A. Texture: Smooth.
- *Sepal shape.*—Apex: Cirrhose. Base: Flat at union with receptacle.
- *Sepal margin.*—Margins have weak or absent foliaceous appendages on three of the five sepals.
- *Sepal size.*—About 30 mm long, 10 mm wide.
- *Receptacle.*—Texture: Smooth. Size: 5 mm in height, 6 mm wide. Color: Yellow-Green Group 144A. Shape: Funnel.
- *Pedicel.*—Surface: Smooth. Length: 65 mm. Diameter: 3 mm on average. Color: Yellow-Green Group 144A. Strength: Strong.
- *Peduncle.*—Length: 4 to 9 cm. Diameter: About 3 mm. Color: Yellow-Green Group 146A. Texture: Smooth.

Flower bud development: Flower buds are borne in clusters of about 3 or 5 flower buds per stem.

Flower bloom:

- *Fragrance.*—Moderate floral.
- *Duration.*—The blooms have a duration on the plant of approximately 21 days. Petals fall cleanly away from plant after flowers have fully matured.
- *Size.*—Flower diameter is 60 to 70 mm when open. Flower depth is 23 mm.
- *Flower shape.*—Hybrid tea like with a tightly closed high center.
- *Shape of flower, side view.*—The upper portion is convex, the lower portion is flat to concave.

Petalage: Under normal conditions, flowers have about 58 petals.

General tonality of flower: Open flowers are Red Group 53A. After 10 days Red Group 53B.

Petal color:

- *Upon opening, outer petals.*—Upper surface: Red Group 53A. Lower surface: Red Group 53A.
- *Upon opening, inner petals.*—Upper surface: Red Group 53A. Lower surface: Red Group 53A.
- *Basal petal spots, upon opening.*—Upper surface: Yellow Group 6C. Lower surface: Yellow Group 6C.
- *After opening, outer petals.*—Upper surface: Red Group 53A. Lower surface: Red Group 53A.
- *After opening, inner petals.*—Upper surface: Red Group 53A. Lower surface: Red Group 53A.
- *Basal petal spots, after opening.*—Upper surface: Yellow Group 6C. Lower surface: Yellow Group 6C.

Petals:

- *Petal reflex.*—Strong bilateral.
- *Margin.*—Entire and uniform. No undulations.
- *Shape.*—Broad and elliptic. Apex shape: Rounded. Base shape: Acute.
- *Size.*—33 mm (l)×41 mm (w).
- *Texture.*—Smooth.
- *Thickness.*—Average.

Petaloids:

- *Size.*—10 mm (l) by 8 mm (w).
- *Quantity.*—About 13.
- *Shape.*—Elliptical with an acute base and rounded apices.
- *Color.*—Red Group 53A with a petaloid spot of Yellow Group 6A.

Reproductive flower parts:

- *Pollen.*—None observed.
- *Anthers.*—Size: 3 mm in length. Color: Yellow Group 9C. Quantity: 35 on average.
- *Filaments.*—Color: Yellow Group 12A. Length: 4 mm.
- *Pistils.*—Length: 8 mm. Quantity: 32 on average.
- *Stigmas.*—Color: Greyed-Yellow Group 162D.
- *Styles.*—Color: Greyed-Yellow Group 162D.
- *Location of stigmas.*—Superior in location relative to the length of the filaments and the height of the anthers.
- *Hips.*—None Observed.

PLANT

Plant growth: Upright. Plants are about 50 cm in height, and 35 cm wide.

Stems:

- *Color of juvenile growth.*—Yellow-Green Group 144B.
- *Color of mature growth.*—Yellow-Green Group 146A.
- *Length.*—Canes are about 32 cm from, the base of the plant to the flowering portion.
- *Diameter.*—About 5 mm.
- *Internodes.*—On mature canes about 35 mm between nodes.
- *Surface texture.*—Young wood: Smooth. Older wood: Smooth.

Long prickles:

- *Incidence.*—9 prickles per 10 cm of stem.
- *Size.*—Average length of prickles on mature stems is 7 mm.
- *Shape.*—Upper portion is linear. Lower portion is concave.
- *Color.*—Juvenile prickles: Yellow-Green Group 144A. Mature prickles: Greyed-Red Group 179C and Yellow-Green Group 146D.

Plant foliage:

- *Compound leaf.*—150 mm (l)×85 (w).
- *Quantity.*—2 or 3 leaves per 10 cm of stem on average.
- *Leaf bearing angle to the stem.*—45 degrees.
- *Color of juvenile foliage.*—Upper side: Yellow-Green Group 144A. Lower side: Yellow-Green Group 144B.

*Color of mature foliage*.—Upper side: Yellow-Green Group 147A. Lower side: Yellow-Green Group 147B.

Plant leaves and leaflets:

*Stipules*.—Size: 11 mm long, 3 mm wide. Quantity: 2 per compound leaf. Shape: Linear, slightly broad based with outward extending apices. Margins: Finely serrated. Color: Yellow-Green Group 144A.

*Petiole*.—Length: 22 mm. Diameter: 2 mm. Upper surface color: Yellow-Green Group 144A. Lower surface color: Yellow-Green Group 144A.

*Rachis*.—Length: About 65 mm. Upper surface color: Yellow-Green Group 144A. Lower surface color: Yellow-Green Group 144A.

*Leaflet*.—Quantity: Normally 7 leaflets. Margins: Serrated. Size: Terminal leaflets are about 62 mm long, 38 mm wide. Shape: Generally elliptical. Base: Obtuse or rounded. Apex: Acuminate. Texture: Rugose. Thickness: Average. Arrangement: Odd pinnate. Venation: Reticulate. Glossiness: Glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant named 'Poulpal103' substantially as described and illustrated herein.

* * * * *

'Poulpal103'

'Poulpal103'